(12) United States Patent
Zanta

(10) Patent No.: US 6,432,279 B1
(45) Date of Patent: Aug. 13, 2002

(54) METHOD AND APPARATUS FOR OZONE GENERATION AND CONTAMINANT DECOMPOSITION

(76) Inventor: Anthony A. Zanta, 3201 Osgood Common, #8, Fremont, CA (US) 94539

(\*) Notice: Subject to any disclaimer, the term of this patent is extended or adjusted under 35 U.S.C. 154(b) by 0 days.

(21) Appl. No.: 09/653,059

(22) Filed: Sep. 1, 2000

Related U.S. Application Data

(60) Provisional application No. 60/153,114, filed on Sep. 7, 1999.

(51) Int. Cl.[7] ............................................... C07C 1/00
(52) U.S. Cl. .............................. 204/157.5; 204/157.44
(58) Field of Search ...................... 204/157.44, 157.5

(56) References Cited

U.S. PATENT DOCUMENTS

| | | | |
|---|---|---|---|
| 3,883,413 A | 5/1975 | Douglas-Hamilton | 204/176 |
| 4,167,466 A | 9/1979 | Orr, Jr. et al. | 204/176 |
| 5,578,280 A | * 11/1996 | Kazi et al. | 422/186.07 |
| 5,756,054 A | * 5/1998 | Wong et al. | 422/186.08 |

\* cited by examiner

*Primary Examiner*—Edna Wong
(74) *Attorney, Agent, or Firm*—Gregory Smith & Associate

(57) ABSTRACT

A method of and apparatus for generating ozone from oxygen or air with irradiation such as from an electron beam. A means for cooling and preferentially positioning oxygen or air to increase ozone yield efficiency and concentration is employed. The disclosed method and apparatus may also be used for other process applications including waste gas and wastewater decontamination.

6 Claims, 5 Drawing Sheets

LEGEND

∽ ELECTRON BEAM
○ OXYGEN MOLECULE
● OZONE MOLECULE

IN-LINE FLUID
PROCESS CHAMBER

METHOD AND APPARATUS FOR OZONE GENERATION AND CONTAMINANT DECOMPOSITION

CROSS REFERENCE TO OTHER APPLICATIONS

This application claims the benefit of U.S. Provisional Patent Application No. 60/153,114, filed Sep. 7, 1999.

FIELD OF THE INVENTION

This invention relates to the production of ozone ($O_3$) and decomposition of contaminants, specifically to methods and apparatus for using density differences in fluids combined with a cylindrically configured irradiation apparatus for improved production of ozone from air or oxygen and for decontamination. Ozone is used as a treatment for drinking water, wastewater, and related applications where it interacts with organic impurities to implement disinfection. Decontamination applications include removal of gaseous pollutants such as sulfur dioxide from effluent gas and volatile organic compound decomposition in water, wastewater, air and other gases.

BACKGROUND OF THE INVENTION

Currently there is only one widely used process for the generation of ozone for water treatment and other commercial uses. This process is referred to as "corona discharge" or "silent discharge". In this process the oxygen or air is introduced to a high voltage environment where the high voltage causes the gas to "corona" at areas of concentrated electric field which leads to break down and arcing between the negative electrode (cathode) and the positive electrode (anode). The products of decomposition of the oxygen include ozone. The corona discharge devices that were first developed have been improved over the years. And now commercially available corona discharge devices can generate a pound of ozone from pure oxygen with as little as 3 kilowatt-hours of energy. Furthermore, the corona discharge process can now convert more than 10 percent of pure oxygen to ozone. Both the energy efficiency and the ozone concentration are critical to the economical production of ozone. In addition to these operating characteristics, ozone generator equipment cost and maintenance are important factors.

Although the corona discharge process has come to be the main method for ozone production, it has its disadvantages and limitations. First of all, relatively large electrode surface areas are required for the corona discharge process. This causes corona discharge reaction chambers to be relatively large and expensive. This large size can also have a significant impact on the space requirements within the user's process facility. Secondly, corona discharge devices require periodic cleaning and replacement of their corona discharge electrodes and insulators in order to minimize system failures. This not only has a labor cost impact, but also has an impact on the floor space needed for access to the system for proper cleaning as well as an impact on the available up time of these systems. Thirdly, corona discharge systems require relatively sophisticated high voltage, high frequency pulsed power supplies to operate. These systems are expensive, complicated and require access to highly qualified technical staff for servicing. And finally, the operating efficiency of the corona discharge device is highly dependent on the availability of low temperature cooling water. This means that in most locations a substantial cost for water chillers must be included in the capital equipment and operating budget for corona discharge systems. In addition, more space, power, and maintenance are required to support the chiller.

Alternative methods for the production of ozone have been reviewed and some have been shown to be viable from the aspect of overall efficiency of production. Steinberg, Beller, and Powell have discussed the advantages of using chemonuclear reactors as an efficient ozone production process. Unfortunately this process may only be cost effective from a capital equipment standpoint for the very largest of water treatment facilities. A number of studies have been made evaluating ozone production rates using either gamma or electron beam radiation. Although these studies have generally shown production efficiencies that equal or exceed corona discharge devices, the capital cost comparisons did not show any economic advantages of these alternatives except for the very largest of systems.

Several patents have been issued for electron beam devices used for the generation of ozone. U.S. Pat. No. 3,883,413 to Douglas-Hamilton (1975) discusses a pulsed discharge electron beam device that generates ozone with the same efficiency that corona discharge systems have today. However this system is not an economical alternative because of its typical ozone concentration of only 0.4%. This is well below the 10 to 15% ozone concentration levels attainable with today's corona discharge systems. U.S. Pat. No. 4,167,466 to Orr, Jr. et al. (1979) describes an electron beam generator with much higher production efficiency. This device requires as little as 0.26 kW-hours of energy to produce a pound of ozone. The patent indicates that high efficiencies are attained by moving oxygen past the beam at high velocities. However the ozone concentrations produced are still less than 1 percent for a single pass through. The patent does indicate much higher ozone production concentrations are possible by repeatedly recycling the oxygen past the beam. However there is no mention of how this can be accomplished cost effectively. U.S. Pat. No. 5,756,054 to Wong et al. (1998) describes an electron beam device that can be used to generate ozone directly from liquid oxygen. This is supported by earlier research that indicated generating ozone concentration levels of up to 10% were generated by an electron beam in liquid oxygen. However the energy dosage had to be applied slowly and the oxygen had to be cryogenically cooled to be maintained in a liquid state. U.S. Pat. No. 5,756,054 discusses an approach that uses cryogenic cooling to separate the ozone from the oxygen. In this way the oxygen not converted to ozone could continue to be processed to maximize ozone production. However it does not address the economics of this process in order to evaluate its cost relative to its benefit.

In summary, a number of corona discharge devices have been used for the production of ozone, but nevertheless they all suffer from a number of disadvantages:

(a) They are large and require considerable space within a facility (b) They require the use of expensive pulsed or high frequency power supplies (c) They require periodic cleaning and other maintenance to function effectively (d) They require water chillers to operate at high efficiencies.

In addition, electron beam generators have been proposed as alternative ozone generating devices, however they also have a number of disadvantages:

(a) Proposed electron beam generators are expensive to manufacture because of their complex configuration and beam focusing requirements.

(b) Their unidirectional or bi-directional beam structure does not allow the system to have the compactness desired for processing systems.

(c) Currently proposed electron beam generators have thus far only generated low concentrations of ozone which may, to some extent be due to recycling limitations.

(d) Additional apparatus proposed for increasing ozone concentrations involving multiple recycling of the oxygen or refrigeration to precipitate ozone are relatively expensive and complicated processes.

A number of patents have been issued for the decomposition of sulfur dioxide and other pollutants using electron beam irradiation. The most important difficulties to overcome for effective irradiation have been penetration of the medium to be processed and spreading the electron beam to effectively process large waste streams. Many innovative techniques have been employed in attempts to overcome these difficulties. For example in U.S. Pat. No. 3,891,855 to Offermann (1975) and U.S. Pat. No. 4,173,719 to Tauber et al. (1979) the process fluid stream is narrowed to allow penetration with a lower energy beam. However converting the fluid stream to a wide, narrow channel can be expensive and cause substantial flow losses and process complications. Other attempts have been made including processing contaminated fluids in the vapor phase as described U.S. Pat. No. 5,319,211 to Matthews et al. (1994). Although penetration of the fluid in the gaseous state is easier, it still requires a complicated flow channel. Furthermore, all electron beam process techniques thus far have been based on treating contaminated fluids where the contaminant is mixed throughout. No effort is made to differentiate and separate the components for preferential processing of only the contaminants.

In summary, electron beam generators have been proposed, and to some extent, used for the removal of sulfur dioxide and other pollutants in the past, however they all suffer from the following disadvantages:

(a) Because of their limited penetration, particularly in denser fluids, the electron beam energy levels must be relatively high which has a direct relationship to their capital cost.

(b) Existing electron beam processors must penetrate and irradiate the entire fluid volume even though the contaminant may be only a small fraction of this volume.

(c) In order to uniformly irradiate fluids with a unidirectional beam, the fluid flow profile must be very flat and wide, which may be expensive to construct for large effluent streams.

(d) The high energy and unidirectional nature of existing electron beam systems necessitates substantial radiation shielding requirements for safety.

SUMMARY OF THE INVENTION

The invention includes apparatus and methods for the production of ozone ($O_3$) and decomposition of contaminants, specifically to a method of using density differences in fluids combined with a cylindrically configured irradiation apparatus for improved production of ozone from air or oxygen and for decontamination. Ozone is used as a treatment for drinking water, wastewater, and related applications where it interacts with organic impurities to implement disinfection. Decontamination applications include removal of gaseous pollutants such as sulfur dioxide from effluent gas and volatile organic compound decomposition in water, wastewater, air and other gases.

A method of and apparatus for generating ozone from oxygen or air with irradiation such as from an electron beam. A means for cooling and preferentially positioning oxygen or air to increase ozone yield efficiency and concentration is employed. The disclosed method and apparatus may also be used for other process applications including waste gas and wastewater decontamination.

Accordingly, several objects and advantages of the present invention for the application of ozone generation are:

(a) to provide a method of ozone generation that preferentially positions the oxygen so that much higher concentrations of ozone can be produced than is possible with the existing technology.

(b) to provide a method of ozone generation that is capable of producing ozone at higher energy efficiencies than is possible with the existing technology.

(c) to provide an ozone generator that is compact and minimizes the space required within a facility.

(d) to provide an ozone generator that uses a simple direct current power supply instead of the pulsed power or high frequency type of device currently used in existing ozone generators.

(e) to provide an ozone generator of which the reaction chamber has virtually no cleaning or maintenance requirements.

(f) to provide an ozone generator that operates effectively without the need for a water chilling device.

(g) to provide an electron beam type ozone generator that does not require the complicated beam focusing systems typically used for unidirectional beam generating devices.

(h) to provide an electron beam type ozone generator that can use a simple, low cost cylindrical chamber geometry similar to standard radio tubes.

A further advantage is to provide an ozone generator which will be able to produce ozone at consistent production levels without the need to perform special tuning of the power supply and reaction chamber as is typically the case for corona discharge devices. Still further objects and advantages will become apparent from a consideration of the ensuing description and drawings.

Regarding embodiments of the invention adapted for use in removing gaseous pollutants, several objects and advantages of the present invention for the destruction of sulfur dioxide and other pollutants and decontamination of fluids are:

(a) To provide a method that can preferentially position sulfur dioxide and other contaminants close to the irradiation source causing them to be decontaminated with a much lower beam energy.

(b) To provide a method that can preferentially position contaminants close to the irradiation source therefore reducing the volume of fluid that must be exposed which reduces the total power needed for contaminant removal or treatment.

(c) to provide an electron beam irradiator that does not require the complicated beam focusing systems typically used for unidirectional beam generating devices.

(d) to provide an electron beam irradiator that can use a simple, low cost cylindrical chamber geometry similar to standard radio tubes.

A further advantage is that because of its low cost configuration, the current invention can be applied to a wider range of pollution treatment applications where irradiation was previously too expensive.

DRAWING FIGURES

In the drawings, closely related figures have the same number but different alphabetic suffixes.

Figure 1:
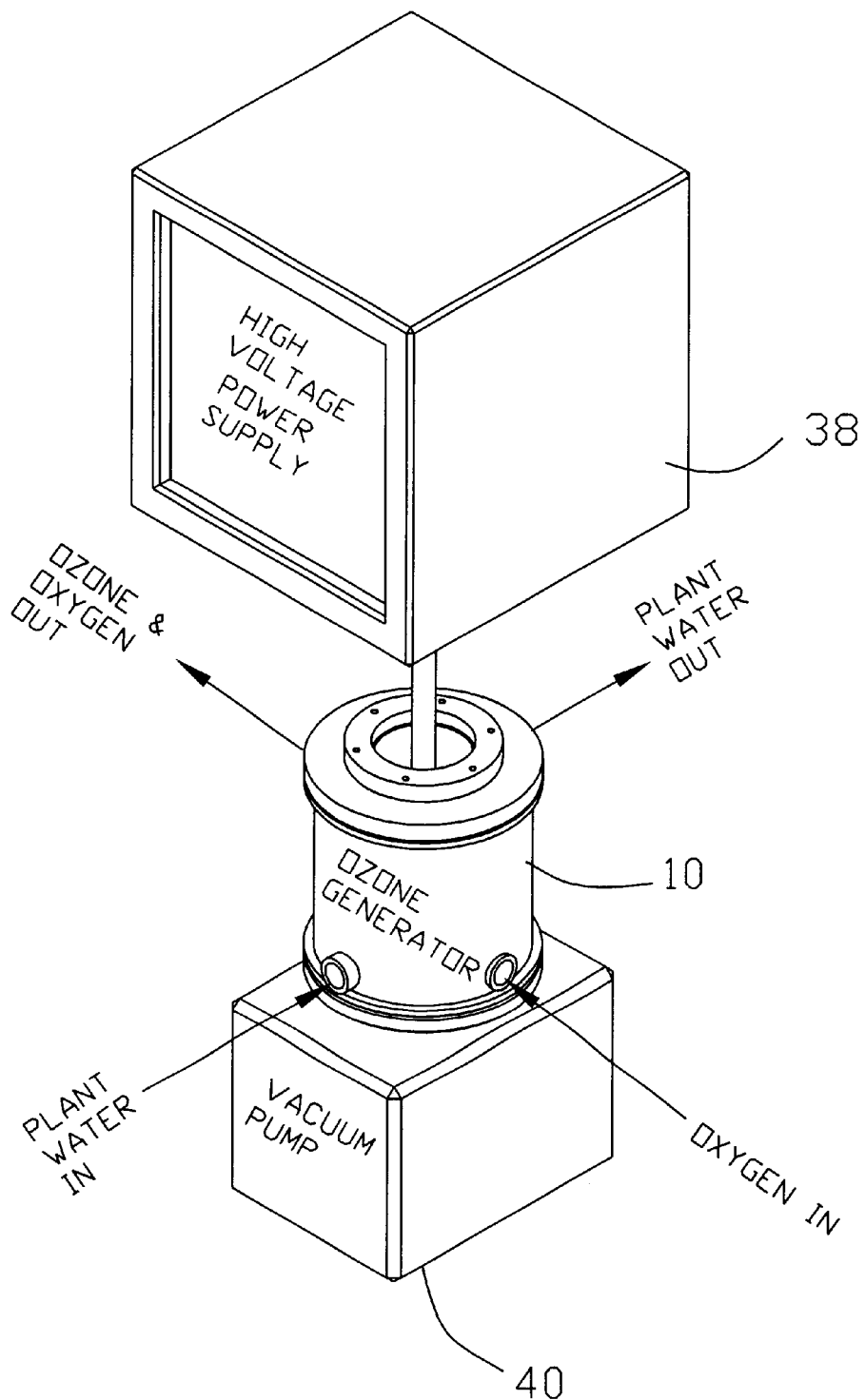
FIG. 1 shows an isometric drawing of an ozone generator operating system.

| Reference Numerals in Drawings: | |
|---|---|
| 10 ozone generator assembly | 12 electron gun mounting plate |
| 14 high voltage insulator bushing | 16 electron gun cathode connection |
| 18 mounting flange | 20 liquid cooling chamber |
| 22 cathode emitter | 24 electron beam window |
| 26 ozone reaction chamber | 28 spiral vane |
| 30 mounting base | 32 cooling liquid inlet port |
| 34 oxygen inlet port | 38 electron gun power supply |
| 40 vacuum pumping system | |

DETAILED DESCRIPTION
Description—FIGS. 1 to 4

Figure 2:
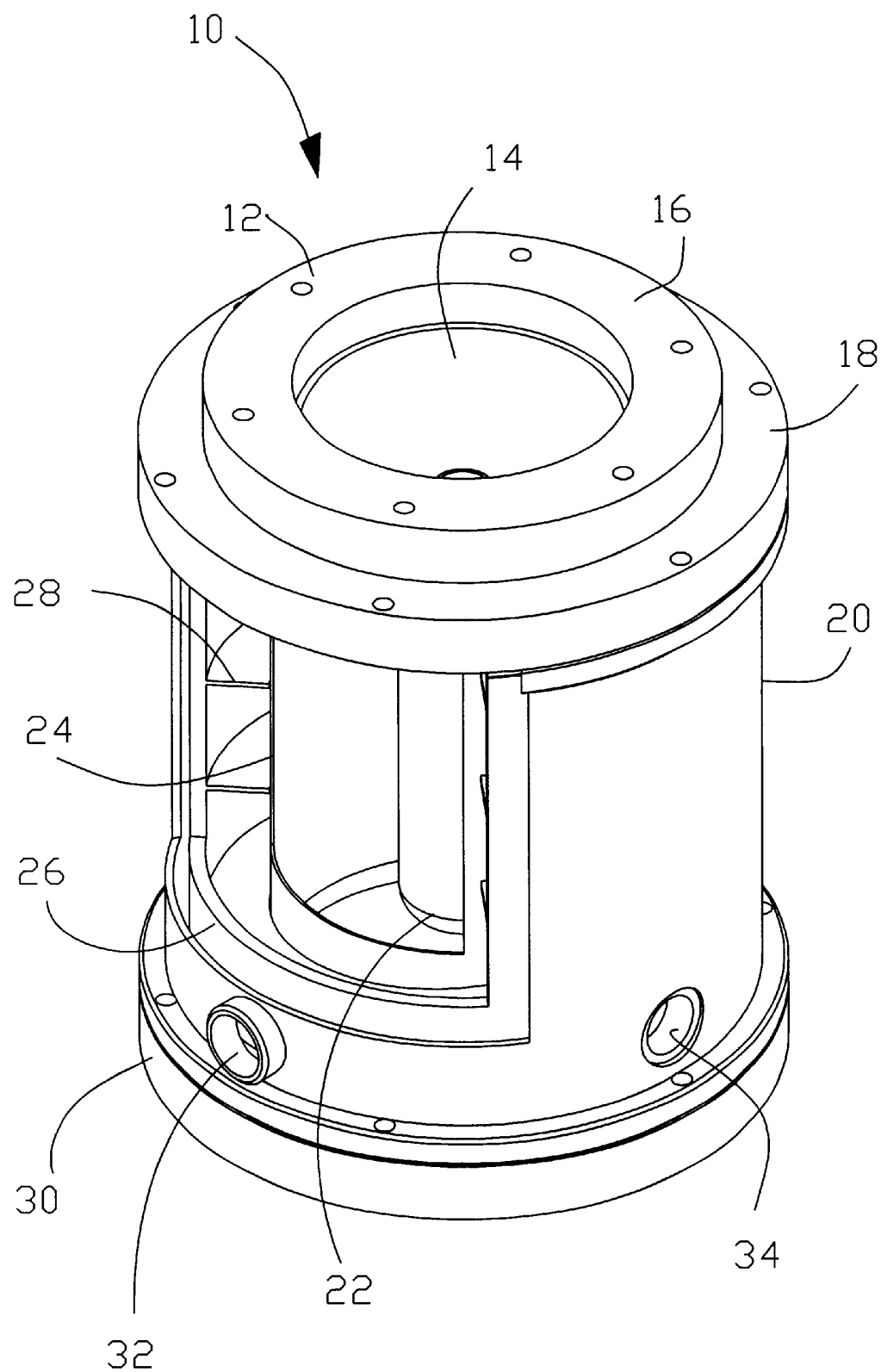
FIG. 2 shows an assembly of an ozone generator chamber with a section removed to illustrate the interior components.

A typical embodiment of an ozone generator of the present invention is illustrated in FIG. 2 (isometric view). The ozone generator assembly 10 has an electron gun mounted in one end of the assembly that is comprised of the electron gun mounting plate 12, high voltage insulator bushing 14, electron gun cathode connection, and a cathode emitter 22. The electron gun cathode emitter 22 is enclosed in a vacuum by the electron beam window 24, and at the ends by the ozone reaction chamber 26. Typically the electron beam window is constructed of thin titanium foil or metallized plastic film. The electron beam window 24 is held in position by soldering or otherwise bonding the window to the spiral vane 28. It lies in an annular space between the electron beam window 24 and the outer wall of the ozone reaction chamber 26. The liquid cooling chamber 20 encloses the ozone reaction chamber 26 and creates an annular cooling passage to cool the ozone reaction chamber 26. The mounting flange 18 and mounting base 30 provide end closures for the vacuum space inside the electron beam window 24 and the liquid cooling chamber 20.

The entire ozone generator assembly 10 is constructed in a cylindrical geometry to minimize its volume and simplify the construction of the device as well as for functional reasons explained below. The cylindrical construction of the cathode emitter and vacuum enclosure is based on well established standard vacuum tube design. The principal difference is that instead of absorbing the current into the anode such as is done with a standard vacuum tube, the current is transmitted through the cylindrical electron beam window 24 into the oxygen gas or other processed fluids outside the window. In one embodiment the cathode emitter 22 is constructed of a cylindrical array of thoriated titanium oxide filaments. Another embodiment consists of an oxide coated cylindrical cathode or cylindrical dispenser cathode. All of these possible embodiments are economic alternatives for radially emitting the electron beam. Typically the cathode emitter diameter is proportional to type of cathode used and the current that must be emitted. In this embodiment the diameter can range from less than 25 millimeters to several hundred millimeters.

The cathode emitter 22 and electron beam window 24 create anode to cathode accelerating space. A negative high voltage in the range of less than 100,000 volts to several hundred thousand volts with respect to ground at the anode is applied to the cathode emitter 22. The gap spacing for electron guns in the voltage range indicated may be less than 25 millimeters to well over 100 millimeters. However because of the superior voltage hold-off characteristics of the coaxial geometry, the gap spacing requirement and consequently the vacuum tube diameter is minimized. The vacuum tube anode diameter is limited mainly by the ability to dissipate the heat deposited in the electron beam window 24. As will be described later, the window is well cooled by rapid flowing process fluid. And this allows much higher energy output per unit area than is possible with corona discharge devices.

An embodiment of this device includes a bias grid surrounding the emitter to regulate the emitted current. The grid bias voltage is generally provided by an additional power supply through the same high voltage insulator bushing 14 that provides the high voltage power for the cathode emitter 22. High voltage cables normally transmit the high voltage power for the cathode emitter 22. In one embodiment of the invention, the high voltage cable is eliminated by connecting the electron gun cathode connection 16 directly to the electron gun power supply 38 (FIG. 1).

One embodiment of this invention is the unique combined construction of the high vacuum enclosed space and electron beam window 24. Typical electron gun systems incorporate a high vacuum chamber constructed of stainless steel with a beam window mounted in one side of the chamber. This typical construction is complicated and expensive. One of the embodiments of this invention is that the electron beam window 24 is cylindrical in shape and forms the entire vacuum space by attaching it to the spiral vane 28. This spiral vane 28 serves several purposes and one of them is to form the cylindrical support for the electron beam window. For fluids that create relatively high pressures on the electron beam window 24, a ring support is placed inside the enclosed vacuum space to internally support the window. To maximize the electron beam transmission into the oxygen or fluid the ring support is formed in the electron beam shadow of the spiral vane 28.

The spiral vane 28 is constructed in a spiral pattern and creates the oxygen or fluid path that is to be processed. The width of the spiral vane is dependent on the heat transfer required to absorb the beam energy and is typically 2 to 20 millimeters wide. The depth of the spiral vane 28 is established by the energy of the beam and the density of the fluid being processed. For liquids this depth may be as small as 0.25 millimeter and for gases the depth may be in excess of 25 millimeters. An important embodiment of this invention is that the depth of the vanes in the reaction chamber is established to insure that most of the beam will be absorbed by the fluid. Very little of the beam should strike the reaction chamber wall in order to maximize ozone production as defined in the operation. Typically the reaction chamber 26 and the spiral vane 28 are constructed of high thermal conductivity metal such as copper or aluminum for more efficient heat transfer. A high conductivity coating such as silver is typically used to protect the surface from corrosion or oxidation without compromising the chamber conductivity.

From the description above, a number of advantages of this ozone generator and fluid processor become evident:

(a) Unlike currently designed ozone generators based on corona discharge, the cylindrical construction of this invention is simple and economical to manufacture.

(b) Electron beam generators have a much higher energy output per unit of surface area, which allows this device to be much more compact than conventional ozone generators.

(c) The power supply for this device can be a standard high voltage direct current unit instead of a pulsed power device. And if pulsed power is desired a relatively simple grid supply can be used to turn the electron beam on and off.

(d) Unlike corona discharge ozone generators, the vacuum tube type of construction has a long history of reliable performance requiring very little maintenance.

(e) Because of the substantially smaller size of this device compared to a corona discharge type system, it is much easier to provide maintenance without the need for special equipment.

(f) By incorporating the centrifuge effect into the process, my generator can selectively direct its energy at oxygen instead of at previously generated ozone leading to the potential to produce much higher concentrations of ozone.

(g) This same centrifuge effect allows selective irradiation which provides the capability to use lower energy, lower capacity electron beams for decontamination than conventional irradiators.

Operation—FIGS 1, 2, 3, 4

In the preferred embodiment of the ozone generator and fluid processor 10 oxygen gas is delivered to the oxygen inlet port 34. The oxygen is typically transferred from an oxygen source such as a cryogenic vessel filled with liquid oxygen. The pressure required to transfer the liquid oxygen is typically generated by the pressure setting on the cryogenic vessel. Once the oxygen enters the oxygen inlet port 34 it then enters the cavity formed by the spiral vane 28 inside the reaction chamber 26 where the oxygen follows in a spiral pattern. An electron beam is emitted from the cathode emitter 22 and is accelerated radially outward from its center by a negative high voltage. The cathode voltage is in the order of 100,000 volts with respect to the outer wall or window where the electron beam exits. This radially directed electron beam has sufficient energy so that the majority of the beam penetrates the cylindrical electron beam window 24 and is deposited into the oxygen gas that is spiraling around the exterior of this window. The electron beam continues to traverse through the oxygen or other fluid and dissipates its energy therein. The electron beam that is deposited into the oxygen has sufficient energy to convert some proportion of it to ozone. Once the ozone and remaining oxygen reach the end of the spiral vane, the two fluids exit the reaction chamber and are transferred to the process requiring the ozone.

In order to produce ozone, tremendous amounts of heat must be deposited into the oxygen. Without the benefit of cooling, the overall temperature of the gas could exceed 1000 degrees Celsius. This excessive temperature would then cause decomposition of the ozone produced leading to limited ozone production. Efficient cooling of the gas is required to prevent this decomposition. The spiral rib pattern of the reaction chamber combined with high velocity flow of the fluid provides the cooling necessary to significantly reduce decomposition of the ozone generated. This flow is typically in the 1000 to 3000 meters per minute for efficient cooling. The heat absorbed by the spiral ribs is transferred into the cooling water or fluid flowing on the exterior of the reaction chamber rib structure.

This high-velocity cooling requirement also creates the added benefit of higher ozone energy conversion efficiency as mentioned in the earlier patent.

Figure 3:
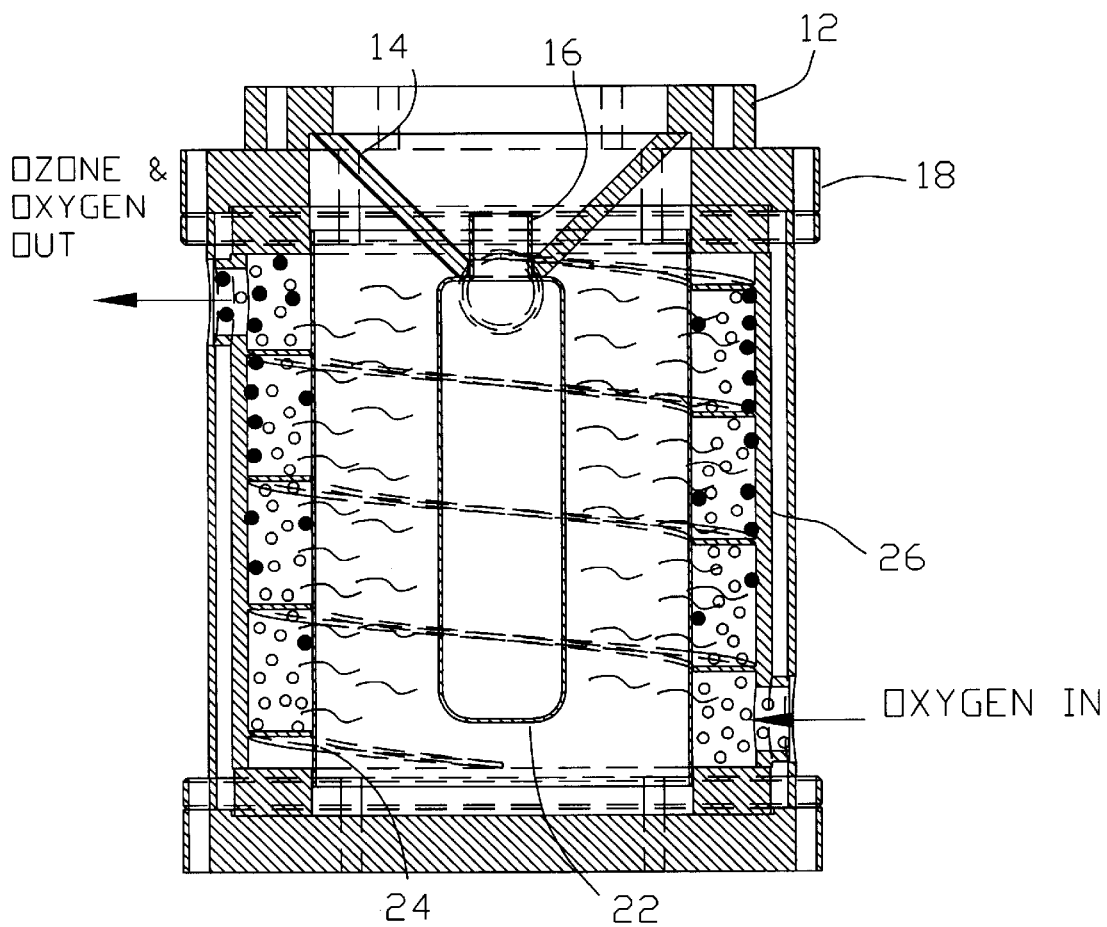
FIG. 3 shows a cross-section of an ozone generator chamber with a depiction of the oxygen conversion to ozone.

The most important characteristic of this method of ozone generation is that the spiral gas flow creates a centrifuge effect. This centrifuge effect causes the oxygen and ozone gases to separate with the newly formed higher density ozone gas moving to the outer edge of the spiral cavity. This separation caused by centrifugal force allows the oxygen to continue to be positioned closest to the incoming electron beam. FIG. 3 shows how the ozone and oxygen move through the generator. The resultant benefit is that the oxygen gas absorbs most of the beam and relatively small amounts penetrate the layer of oxygen gas to strike the outer layer of ozone just produced. This combined effect of high velocity flow and centrifugal force created with the spiral motion creates the potential for unprecedented concentrations of ozone while still maintaining high-energy efficiency ozone production.

In summary, the key to high efficiency ozone production by electron beam is high velocity oxygen flow past the beam. And the key to producing high concentrations of ozone is recycling the oxygen while separating the generated ozone to prevent its decomposition. The method of spiral gas flow of this invention allows these key events to occur simultaneously and also is the key to the removal of high levels of generated heat. And the unique cylindrical radial electron beam pattern with its inherent compact beam geometry facilitates the employment of this unique ozone production process.

This same method can be employed for processing other fluids as well. The key is that the fluids that require processing must have a significant density difference than the other fluids in the stream. There are some differences in operation, but the principles are the same. For example, sulfur dioxide, ($SO_2$) has a significantly higher density than the other gases in a smokestack effluent stream. In this instance, since the gas to be irradiated is denser than the other gases, the electron beam geometry has to be radiated towards the center of the axis instead of outward. Another major difference is that the heat dissipation requirements are much lower than for ozone production. Therefore there may not be a requirement for facility cooling.

Figure 4:
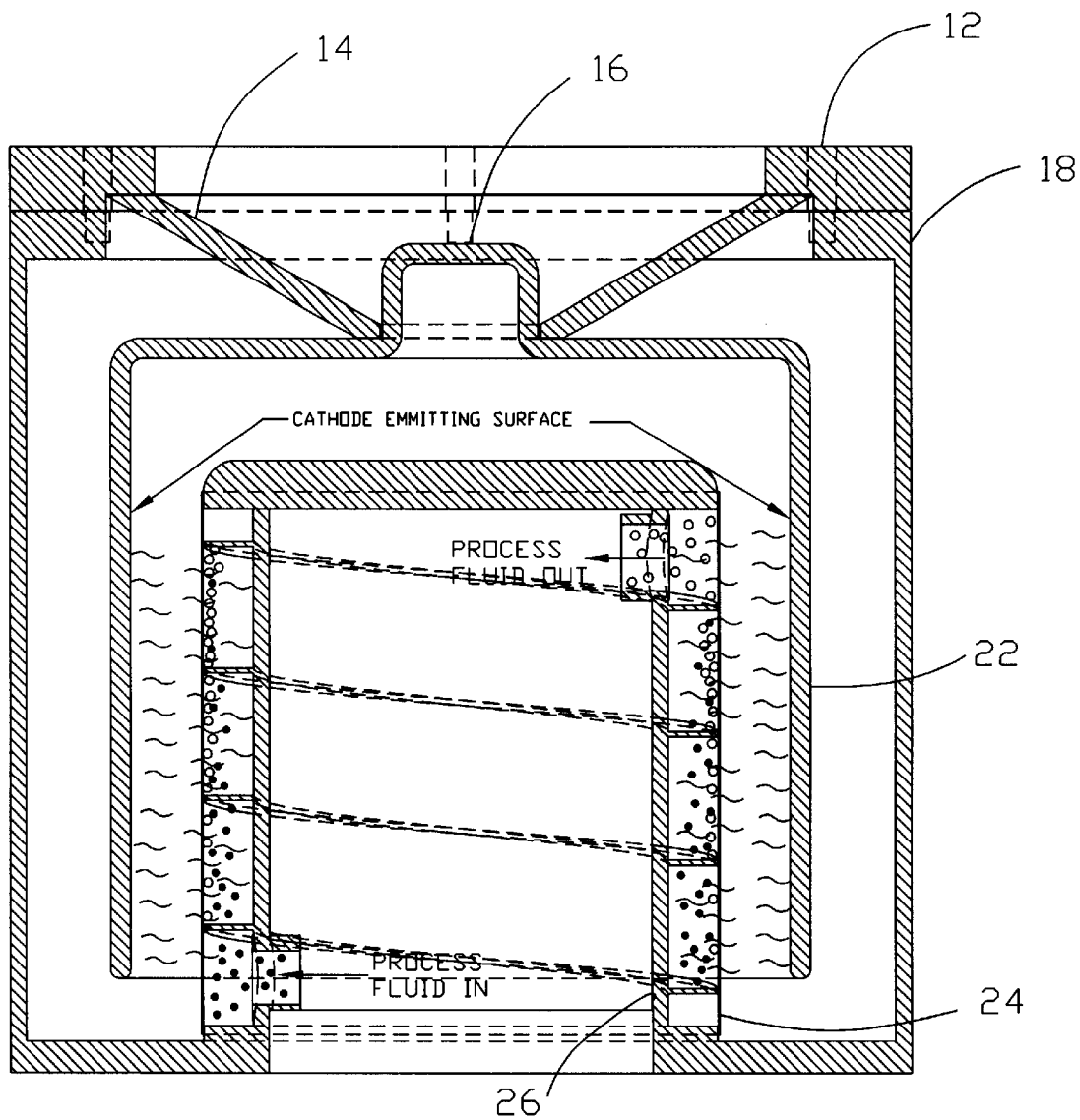
FIG. 4 shows a cross-section of a fluid treatment device with a depiction of the pollutant decomposition.

FIG. 4 shows an embodiment of this invention to decompose a pollutant. In this example it is assumed that the pollutant to be decomposed is denser than the other gases in the flow stream, and that no additional cooling is required. In this embodiment the cathode is shown radiating inward. The pollutant as well as the other gases are fed into the spiral vane chamber 26 which in this case shows the chamber wall inboard. The electron beam window 24 attaches on the outer edge of the spiral vane 28. As the gas or fluid flows in the spiral pattern, centripetal force causes the denser pollutant to flow to the outer wall, which is in this case, is the electron beam window 24. The inward radiating electron beam therefore is mainly absorbed in the pollutant causing it to decompose or otherwise be altered to an acceptable state. This process substantially reduces the power required because a much smaller percentage of fluid is processed, and the beam penetration requirements are much lower.

Figure 5:
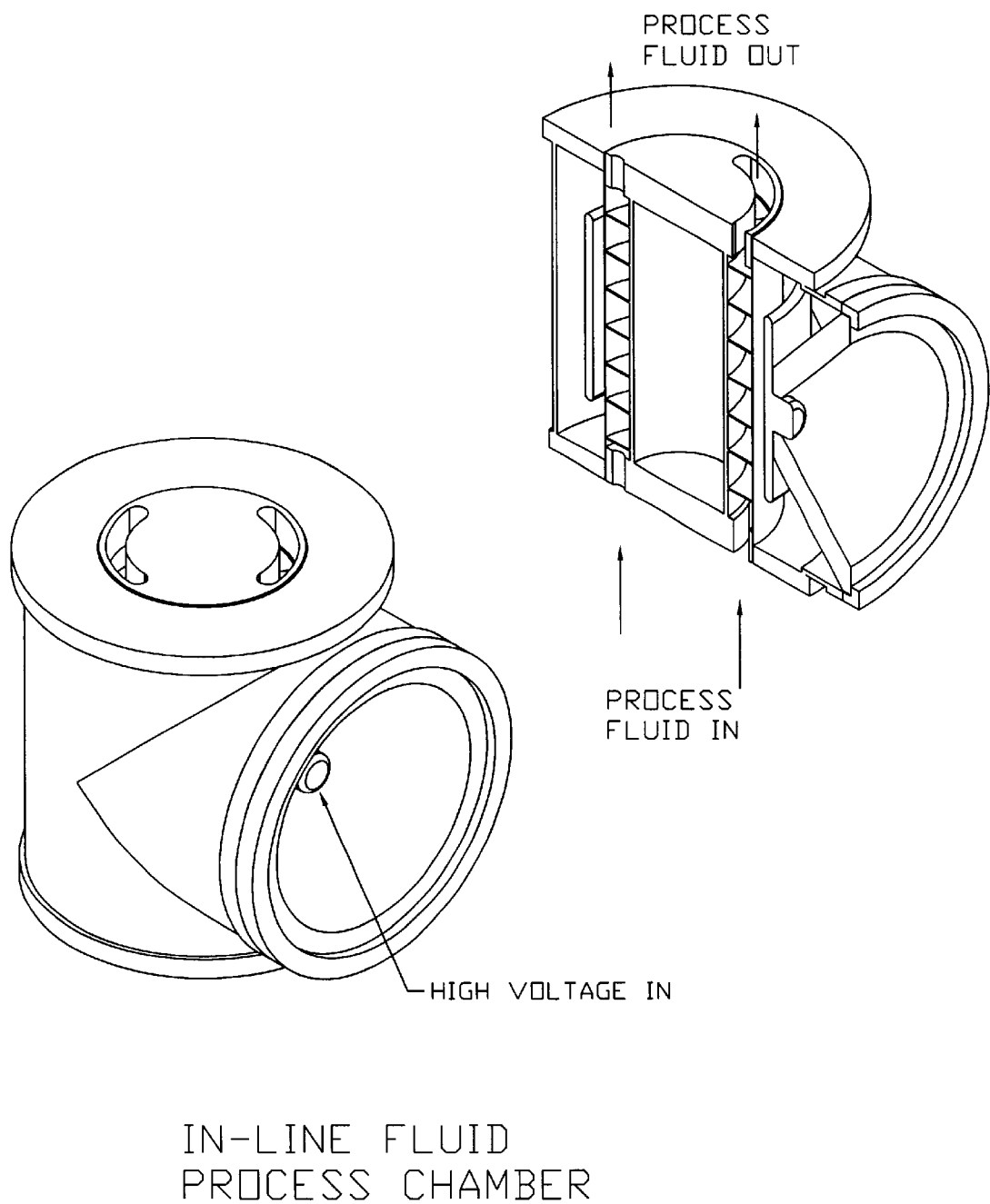
FIG. 5 shows a device.

The inward radiating electron beam generator configuration shown in FIG. 4 can have other variations. For example for stack gases where it is desirable to minimize flow interruptions and discontinuities, a spiral vane can be mounted axially in the beam path so that the gas flows directly out of its pipe, through the spiral vane, and back into pipe of the same diameter. FIG. 5 shows an example of this kind of device.

In summary, the method of spiraling the fluid to create the centrifuge action, coupled with the unique circular geometry of the irradiator that allows radiation inward as well as outward provides a unique alternative for cost effective processing with electron beam. By concentrating and isolating the fluid to be treated, a substantial reduction in both power requirements and capital equipment requirements is attained.

Accordingly, the reader will see that the ozone generator of this invention can be used to produce ozone efficiently and economically. And because of the processes incorporated and its unique geometry it has the potential to attain much higher ozone concentrations more efficiently than existing ozone generating devices. These advantages mean that both less power and less oxygen are required than corona discharge devices to generate the same quantities of ozone. As a processor for contaminated fluids the invention has the further advantages that it only requires a fraction of the voltage that conventional electron beam processors require. And since it does not need to process the entire fluid stream, it requires only a fraction of the throughput normally required for such a device. Furthermore the ozone generator and fluid processor apparatus has the following additional advantages:

Because of its simple construction, it can be manufactured at a considerably lower cost than corona discharge ozone generating devices.

It is much smaller than existing corona discharge generating devices and can therefore be more easily installed in limited spaces.

It is powered by much simpler dc power supplies that are less expensive to build than medium to high frequency or pulsed power supplies that are now used for existing ozone generators.

It requires little or no cleaning and maintenance because there are no corona discharge components that wear and must be periodically cleaned and replaced.

Unlike existing ozone generators, there is no requirement for expensive chilled water equipment that will take up valuable plant operating space to support efficient production of ozone.

It allows the use of standard vacuum tube cylindrical geometry, a much lower cost construction than unidirectional electron beam generating devices.

Although the description above has been directed at describing particular embodiments of the method and device in accordance with the patent requirements, it should not be construed as limiting the scope of the invention but as merely providing illustrations of some of the presently preferred embodiments of this invention. For example, a pulsed power high voltage supply can be used instead of a dc supply. The cathode emitter can be square or rectangular instead of cylindrical. The high voltage insulator bushing can be tapered in a different direction than what is shown. The spiral vane can be a group of vanes in either a spiral pattern or in a cylindrical pattern that move the fluid in parallel with one another around the electron beam window. The oxygen can be directed into any flow pattern that achieves the preferred orientation of the oxygen closest to the beam and the ozone farthest from the beam. For fluid process streams where the pollutants to be treated are denser than the fluid, the irradiation is directed inwards as shown in FIG. 4.

It should also be noted that this electron beam device can be used for a number of other applications where the benefit of electron beam processing combined with the centrifuge effect facilitate the preferential processing of dissimilar density materials. As previously mentioned, the dissimilar densities of exhaust or smokestack gases can allow the different density gases to be preferentially processed by the electron beam. For example, for denser gases such as sulfur dioxide, the centrifuge effect of spiraling the gas causes it to move to the outermost section of the reaction chamber. This then requires the irradiation device to be directed inward to decompose the sulfur dioxide gas as shown in FIGS. 4 and 5.

As also mentioned, this process is also applicable to liquids such as water and other fluids which may contain contaminants that are at different densities than the main fluid stream. One specific application is for irradiating suspended solids in a liquid. By using the centrifuge effect caused by spiraling the fluid with its suspended solids, the solids which are denser move outward in the spiraled fluid stream and are therefore irradiated by a process beam such as shown in FIG. 4.

Another application that this can be used for is radiation curing. For example, polymers that are to be applied are often transferred in a solvent that is of lower density. The process of spiraling the polymer that must be cured past an irradiator prior to its being applied to a substrate may save considerable curing costs. In this case since the polymer is denser than the solvent carrying it, it is forced against the outside wall and is therefore preferentially treated by an inward electron beam device such as depicted in FIG. 4.

Another application is for fluid sterilization when there is a mixture of fluids that have significantly different densities. If only one of the fluids requires irradiation for pasteurization or sterilization, this component can be preferentially positioned to the outer wall if it is denser whereby the device in FIG. 4 would be applicable. If the fluid to be treated was a lower density than the other fluid or fluids, this lower density material would migrate to the inner wall of the spiral chamber and would therefore be irradiated with an outwardly directed beam as shown in FIG. 3.

Food pasteurization with an irradiation source is also an application for which this device can be used. For example if a food component that needs to be treated is of a different density than other components within the food mixture, the particular component requiring treatment can be separated using the centrifuge effect so that it can be positioned closest to the irradiation source. If it is denser than the rest of the food ingredients it will migrate towards the outermost perimeter of the spiral path and will thus be irradiated with the inward pattern beam as shown in FIG. 4. If it is lighter than the rest of the food components it will migrate towards the innermost area of the spiral path so that it can be irradiated with the outwardly oriented beam.

There are many other applications of how this process and device can be used that are not enumerated here. Thus the scope of the invention should be determined by the appended claims and their legal equivalents, rather than by only the examples given.

I claim:

1. A method for improving ozone production by irradiation from a gas comprising oxygen, the method comprising the steps of:
    (a) flowing said gas comprising oxygen and formed ozone by means of a pressurized force into a path surrounding an irradiation source, said path including an inner perimeter and an outer perimeter;
    (B) simultaneously exposing said gas comprising oxygen to said irradiation source whereby it is irradiated to produce ozone;
    (C) simultaneously cooling said gas comprising oxygen to reduce ozone decomposition; and (D) simultaneously causing higher density formed ozone to move toward said outer perimeter of said path whereby said ozone receives lower levels of irradiation to minimize ozone decomposition and causing lower density oxygen in said oxygen containing gas to move toward said inner perimeter of said path whereby said lower density oxygen receives higher levels of irradiation to improve ozone production.

2. The method of claim 1, wherein said irradiation source is an electron beam source, x-ray source, or gamma ray source irradiating outwards from inside said path surrounding said irradiation source.

3. The method of claim 1, wherein said pressurized force is generated by a liquid oxygen reservoir or compressor that causes said oxygen to flow at a desired rate.

4. The method of claim 1, wherein said path surrounding said irradiation source comprises a curvilinear path in a cylindrical or spiral or similarly formed path that causes centripetal force to act on said oxygen containing gas, whereby said higher density formed ozone is caused to move toward said outer perimeter of said path and said lower density oxygen in said oxygen containing gas is caused to move toward said inner perimeter of said path.

5. The method of claim 1, wherein said oxygen containing gas is cooled by transferring heat from said oxygen containing gas to cooled surfaces defining said path and that have sufficient surface area when combined with said movement of said oxygen containing gas along said path to limit temperature to an allowable maximum for decomposition.

6. A method for improving ozone production by irradiation from a gas comprising oxygen, the method comprising the steps of:
   (a) flowing said gas comprising oxygen by means of a pressurized force into a path surrounding an irradiation source, said path including an inner perimeter and an outer perimeter;
   (b) simultaneously with step (a) exposing said gas comprising oxygen to said irradiation source whereby it is irradiated to produce ozone;
   (c) simultaneously causing higher density formed ozone to move toward said outer perimeter of said path, and causing lower density oxygen in said oxygen containing gas to move toward said inner perimeter of said path.

* * * * *

UNITED STATES PATENT AND TRADEMARK OFFICE
CERTIFICATE OF CORRECTION

PATENT NO.      : 6,432,279 B1
DATED           : August 13, 2002
INVENTOR(S)     : Anthony A. Zante It is certified that error appears in the above-identified patent and that said Letters Patent is hereby corrected as shown below:

<u>Title page,</u>
Item [12], Inventor's last name, please change "Zanta" to -- Zante --.
Item [76], Inventor, please change "Anthony A. Zanta" to -- Anthony A. Zante --

Signed and Sealed this

Fourth Day of March, 2003

JAMES E. ROGAN
*Director of the United States Patent and Trademark Office*